United States Patent [19]

Leppard

[11] 4,452,884
[45] Jun. 5, 1984

[54] COLOR-PHOTOGRAPHIC RECORDING MATERIAL

[75] Inventor: David G. Leppard, Rheinfelden, Switzerland

[73] Assignee: Ciba-Geigy AG, Basel, Switzerland

[21] Appl. No.: 450,513

[22] Filed: Dec. 17, 1982

[30] Foreign Application Priority Data

Dec. 17, 1981 [CH] Switzerland ............ 8067/81

[51] Int. Cl.³ .................................... G03C 7/26
[52] U.S. Cl. .......................... 430/551; 430/372; 430/523; 430/961
[58] Field of Search ........... 430/551, 523, 372, 961

[56] References Cited

U.S. PATENT DOCUMENTS

| | | | |
|---|---|---|---|
| 2,596,926 | 5/1952 | Gunther et al. | 430/372 |
| 3,183,219 | 5/1965 | Schuler | 430/512 |
| 4,148,784 | 4/1979 | Malherbe et al. | 260/45.8 N |
| 4,268,593 | 5/1981 | Leppard et al. | 430/551 |

*Primary Examiner*—J. Travis Brown
*Attorney, Agent, or Firm*—Wenderoth, Lind & Ponack

[57] ABSTRACT

A color-photographic recording material which, in at least one light-sensitive silver halide emulsion layer, an interlayer and/or a protective layer, contains at least one polyalkylpiperidine compound of the formula I

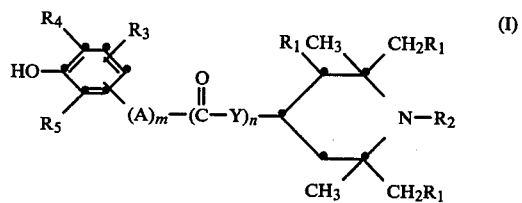

as a light stabilizer.

Color images obtained by imagewise exposure and development of this color-photographic recording material display good stability to the action of visible and ultra-violet light.

With respect to the definitions of the substituents and symbols in formula I, reference is made to the specification.

9 Claims, No Drawings

COLOR-PHOTOGRAPHIC RECORDING MATERIAL

The present invention relates to a colour-photographic recording material which, in at least one light-sensitive silver halide emulsion layer and/or in at least one of the conventional auxiliary layers, contains at least one polyalkylpiperidine light-stabiliser.

In European Patent Application No. 11,051, a colour-photographic recording material has already been described, which contains a polyalkylpiperidine light-stabiliser in order to improve the lightfastness of the colour images obtained with this material and to suppress undesired fogging.

It has now been found that, surprisingly, an even better light-stabilising effect can be achieved when the compounds of the formula I, described below, are incorporated into the colour-photographic recording material.

The present application therefore relates to a colour-photographic recording material which, in at least one light-sensitive silver halide emulsion layer, an interlayer and/or a protective layer, contains at least one polyalkylpiperidine compound as a light stabiliser, wherein the polyalkylpiperidine compound is of the formula I

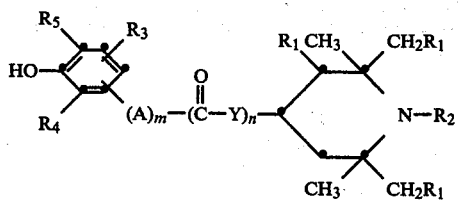

in which $R_1$ and $R_3$ independently of one another are hydrogen or methyl, $R_2$ is hydroxyl, $C_1$–$C_{12}$-alkyl, $C_3$–$C_{12}$-alkenyl, $C_3$–$C_4$-alkynyl, 2-hydroxyethyl, $C_2$–$C_{11}$-alkoxyalkyl, $C_7$–$C_{14}$-aralkyl or a group of the formula —$(CH_2)_p$—$CH(R_6)$—$X_1$ or —$CH(R_6)$—$X_2$, in which p is one of the numbers 1, 2 or 3, $X_1$ is halogen, cyano, —$OR_7$, —$OC(O)R_7$, —$OC(O)N(R_7)(R_8)$, —$C(O)OR_7$ or —$C(O)N(R_7)(R_8)$, $X_2$ is halogen, cyano, 1,2-epoxyethyl, —$C(O)OR_7$ or —$C(O)N(R_7)(R_8)$ and $R_6$ is hydrogen, methyl or phenyl, $R_7$ being hydrogen, $C_1$–$C_{12}$-alkyl, $C_2$–$C_{12}$-alkenyl, $C_3$–$C_{12}$-cycloalkyl, phenyl, $C_7$–$C_{14}$-alkaryl or $C_7$–$C_{14}$-aralkyl and $R_8$ being hydrogen or $C_1$–$C_4$-alkyl, or $R_7$ and $R_8$, together with the nitrogen atom to which they are bonded, forming a 5-membered or 6-membered heterocyclic ring, or $R_2$ is a group of the formula II $$L—CO— \quad (II)$$

in which L is hydrogen, $C_1$–$C_{12}$-alkyl, $C_2$–$C_{12}$-alkenyl, $C_3$–$C_4$-alkynyl, $C_3$–$C_{12}$-cycloalkyl, $C_7$–$C_{14}$-alkaryl, $C_7$–$C_{14}$-aralkyl, chloromethyl, unsubstituted phenyl, phenyl which is substituted by two $C_1$–$C_4$-alkyls and one hydroxyl, or a group —$OR_9$, in which $R_9$ is $C_1$–$C_{12}$-alkyl, cyclohexyl, $C_2$–$C_{12}$-alkenyl, benzyl or phenyl, or L is a group of the formula III

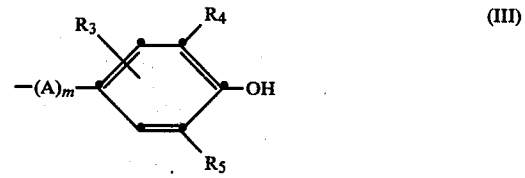

or $R_2$ is a group of the formula IV

in which $R_{10}$ and $R_{11}$ independently of one another are $C_1$–$C_{12}$-alkyl, $C_3$–$C_{12}$-alkenyl, $C_3$–$C_{12}$-cycloalkyl, phenyl, $C_7$–$C_{14}$-alkaryl or $C_7$–$C_{14}$-aralkyl and $R_{11}$ additionally can also be hydrogen, or $R_2$ is a group of the formula V

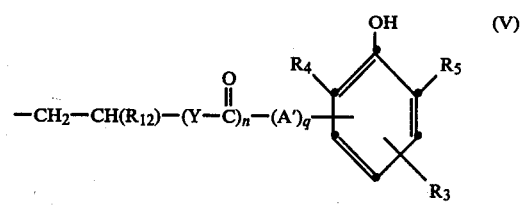

in which A' is methylene or a group —$CH_2$—$CH(R_{13})$— and q is zero or 1, and $R_{12}$ and $R_{13}$ independently of one another are hydrogen, methyl, ethyl, phenoxymethyl or phenyl, or $R_2$ is a group of the formula VI

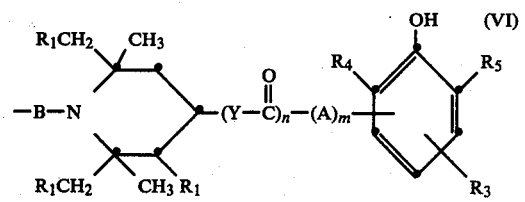

in which B is a group $C_rH_{2r}$, in which r is a number from 2 to 12, or is $C_4$–$C_8$-alkenylene, $C_4$–$C_8$-alkynylene, phenylene, xylylene, bitolylene, $C_5$–$C_{12}$-cycloalkylene or a group —$CONH$—$B_1$—$NHCO$—, in which $B_1$ is a group $C_rH_{2r}$, phenylene, naphthylene, tolylene or a group of the formulae

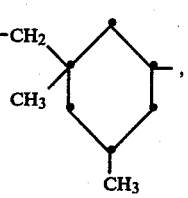

,

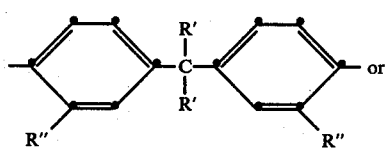

or

-continued

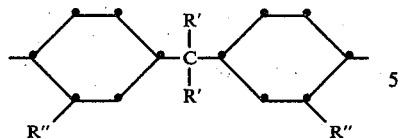

in which R' is hydrogen, methyl or ethyl, R" is hydrogen or methyl and r is as defined above, or $R_2$ is one of the groups $-S(O)_zR_{14}$ or $-OR_{15}$, in which z is the number 1 or 2, $R_{14}$ is $C_1-C_{12}$-alkyl, $C_7-C_{14}$-alkaryl or phenyl and $R_{15}$ is $C_1-C_{12}$-alkyl, $C_3-C_{12}$-alkenyl, $C_7-C_{14}$-aralkyl or a group of the formula L'—CO—, in which L' is as defined above for L, $R_4$ and $R_5$ independently of one another are $C_1-C_{12}$-alkyl, $C_3-C_{12}$-cycloalkyl, $C_7-C_{14}$-aralkyl, $C_7-C_{14}$ alkaryl or phenyl and $R_4$ can additionally also be hydrogen or a group of the formula Ia

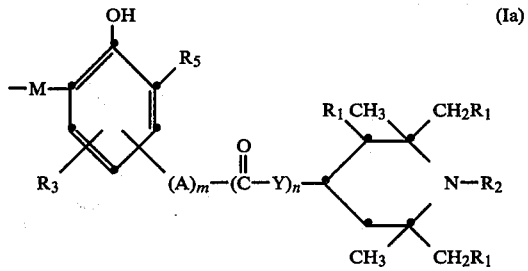

in which $R_1$, $R_2$, $R_3$, $R_5$, A, Y, m and n are as defined and M is a direct bond,

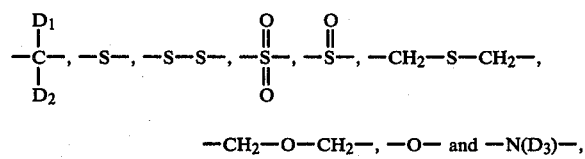

$-CH_2-O-CH_2-$, $-O-$ and $-N(D_3)-$, and $D_1$ and $D_2$ independently of one another are hydrogen, $C_1-C_{18}$-alkyl, alkyl interrupted by 1 to 3 —S— or phenyl, or $D_1$ and $D_2$, together with the C atom linking them, form a 5-membered or 6-membered aliphatic ring and $D_3$ is hydrogen, $C_1-C_{18}$-alkyl or phenyl, Y is —O— or $-N(R_{16})-$, in which $R_{16}$ is hydrogen, $C_1-C_{18}$-alkyl, $C_3-C_{12}$-alkenyl, $C_3-C_{12}$-cycloalkyl, phenyl, $C_7-C_{14}$-alkaryl, $C_7-C_{14}$-aralkyl, $C_3-C_{11}$-alkoxyalkyl, a group of the formula VII

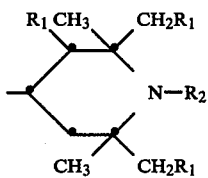

or a group —Z—D, in which Z is a $-(CH_2)_s$ group unsubstituted or substituted by a methyl group, s being one of the numbers 2 to 4 and D being hydroxyl, $-OR_{17}$ or $-N(R_{18})(R_{19})$, in which $R_{17}$ and $R_{18}$ are hydrogen, $C_1-C_{12}$-alkyl, $C_3-C_{12}$-cycloalkyl or a group of the formula VIII

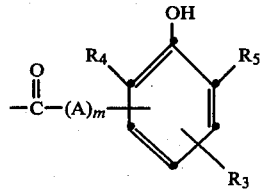

and $R_{17}$ additionally can also be a group of the formula VII, $R_{19}$ is hydrogen, $C_1-C_{12}$-alkyl, $C_3-C_{12}$-cycloalkyl or a group of the formula IX

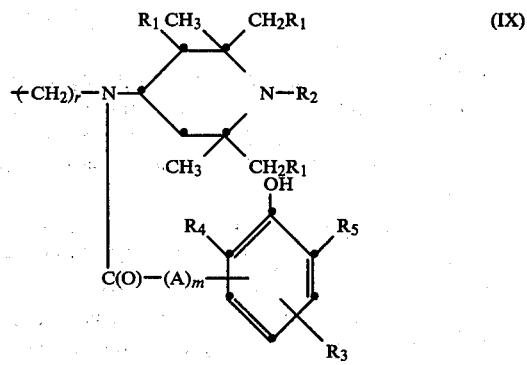

or $R_{18}$ and $R_{19}$, together with the nitrogen atom to which they are bonded, form a 5-membered or 6-membered heterocyclic ring, or $R_{16}$ is a group of the formula IXa

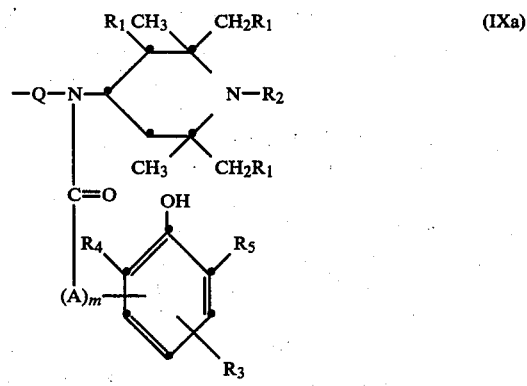

in which Q is as defined above for B, n and m independently of one another are zero or 1, and A is methylene or a group $-CH_2-CH(R_{20})-$ or $-CH_2-C(E)(G)-$, in which $R_{20}$ is hydrogen, methyl, ethyl, phenoxymethyl or phenyl, E is cyano or a group $-C(O)OR_{21}$, $-C(O)R_{22}$, $-SO_2R_{22}$, $-P(O)-(OR_{23})_2$, $-C(O)NR_{24}R_{25}$ or —CHO, in which $R_{21}$ is $C_1-C_4$-alkyl, $R_{22}$ is $C_1-C_{12}$-alkyl, $C_7-C_{14}$-alkaryl or phenyl, $R_{23}$ is $C_1-C_{18}$-alkyl, phenyl or allyl, and $R_{24}$ and $R_{25}$ independently of one another are hydrogen, $C_1-C_{18}$-alkyl or phenyl, and G is hydrogen, $C_1-C_{18}$-alkyl, $C_3-C_{12}$-alkenyl, $C_3-C_4$-alkynyl, $C_5-C_{12}$-cycloalkyl, $C_6-C_{18}$-alkylcycloalkyl, $C_6-C_{14}$-cycloalkylalkyl, $C_7-C_{14}$-aralkyl, $C_7-C_{19}$-alkylaralkyl, phenyl, or $C_1-C_{18}$-alkyl which is substituted by phenoxy, $C_7-C_{10}$-alkylphenoxy, benzyloxy, cyclohexyloxy, cyano, $-COOR_{26}$, $-OCOR_{27}$ or $-P(O)(OR_{28})_2$, $R_{26}$ being $C_1-C_{18}$-alkyl, $C_3-C_{12}$-cycloalkyl or a group of the formula VII, $R_{27}$ being $C_1$–$C_{18}$-alkyl, $C_3$–$C_{12}$-cycloalkyl, phenyl, $C_7$–$C_{14}$-aralkyl or a group of the formula III and $R_{28}$ being $C_1$–$C_{18}$-alkyl, allyl or phenyl, or G is $C_2$–$C_{18}$-alkyl interrupted by —O—, —S—, —SO— or —SO$_2$—, a group of the formula VII or a group of the formula

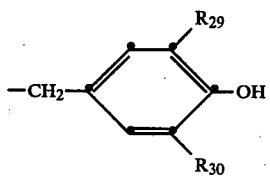

in which $R_{29}$ and $R_{30}$ independently of one another are $C_1$–$C_4$-alkyl and $R_{30}$ additionally can also be hydrogen, or, if E is a group —C(O)R$_{22}$, G and $R_{22}$ together are trimethylene or tetramethylene.

$C_1$–$C_{12}$-Alkyl substituents which may be present can be branched or unbranched alkyl, for example methyl, ethyl, n-propyl, isopropyl, n-butyl, sec.-butyl, tert.-butyl, n-pentyl, n-hexyl, n-octyl, 1,1,3,3-tetramethylbutyl, n-nonyl, decyl or dodecyl. $C_1$–$C_4$-Alkyl is preferred. $C_1$–$C_{18}$-Alkyl radicals $R_{16}$ and $R_{23}$ can additionally be, for example, tridecyl, tetradecyl, hexadecyl or octadecyl.

$C_1$–$C_4$-Alkyl substituents which may be present are methyl, ethyl, n-propyl, isopropyl, n-butyl, sec.-butyl or tert.-butyl.

$C_3$–$C_{12}$-Alkenyl substituents which may be present are, for example, allyl, methallyl, 2-butenyl, 2-hexenyl, 2-octenyl, 4-octenyl, 2-decenyl or 2-dodecenyl. Allyl is preferred. $C_2$–$C_{12}$-Alkenyl substituents can additionally also be vinyl. In this case, vinyl and allyl are preferred.

$C_3$–$C_4$-Alkynyl radicals $R_2$, G and L are, for example, propargyl, n-but-1-ynyl or n-but-2-ynyl. Propargyl is preferred.

$C_3$–$C_{11}$-Alkoxyalkyl radicals $R_2$ and $R_{16}$ are, for example, ethoxymethyl, 2-methoxyethyl, 2-ethoxyethyl, 2-n-butoxyethyl, 2-n-butoxypropyl, 2-n-octoxyethyl, 3-n-octoxypropyl or 6-n-butoxyhexyl. Additionally, a $C_2$-alkoxyalkyl radical $R_2$ can also be methoxymethyl.

Halogens $X_1$ and $X_2$ are, for example, bromine, iodine and in particular chlorine.

$C_3$–$C_{12}$-Cycloalkyl substituents which may be present are, for example, cyclopropyl, cyclopentyl, cyclohexyl, cycloheptyl, α-methylcyclohexyl, cyclooctyl, cyclononyl, cyclodecyl or cyclododecyl. Cyclohexyl is preferred.

$C_7$–$C_{14}$-Alkaryl substituents which may be present are, for example, phenyl substituted by $C_1$–$C_4$-alkyl, such as p-tolyl, 2,4-dimethylphenyl, 2,6-dimethylphenyl, 2,4-diethylphenyl, 2,6-diethylphenyl, 4-tert.-butylphenyl, 2,4-di-tert.-butylphenyl or 2,6-di-tert.-butylphenyl. 2,4-Di-tert.-butylphenyl and 2,4-dimethylphenyl are preferred.

5-Membered or 6-membered heterocyclic rings, formed by $R_7$ and $R_8$ or $R_{18}$ and $R_{19}$ together with the nitrogen atom to which they are bonded, are, for example, pyrrolidine, oxazolidine, piperidine or morpholine radicals.

$C_7$–$C_{14}$-Aralkyl substituents which may be present are, for example, benzyl, p-methylbenzyl, p-tert.-butylbenzyl, 1-phenylethyl, α,α-dimethylbenzyl or 2-phenylethyl.

In —$C_rH_{2r}$— groups B, $B_1$ or Q, in which r is a number between 1 and 12, r preferably is a number between 2 and 8. Examples are methylene, ethylene, trimethylene, tetramethylene, hexamethylene, octamethylene, nonamethylene, 2,2,4-trimethylhexamethylene, decamethylene and dodecamethylene.

$C_4$–$C_8$-Alkenylene radicals B or Q are, for example, but-2-en-1,4-ylene.

$C_4$–$C_8$-Alkynylene radicals B or Q are, for example, but-2-yn-1,4-ylene.

$C_5$–$C_{12}$-Cycloalkylene radicals B and Q are, for example, cyclopentylene, cyclohexylene, cyclooctylene, cyclodecylene or cyclododecylene. Cyclohexylene is preferred.

$C_1$–$C_{12}$-Alkyl radicals G, substituted by phenoxy, benzyloxy, cyclohexyloxy or cyano, can, for example, be one of the following radicals: 2-phenoxyethyl, 2-benzyloxyethyl, cyclohexyloxymethyl, 2-cyanoethyl, cyanomethyl or 3-cyanopropyl.

$C_6$–$C_{18}$-Alkylcycloalkyl radicals G are, for example, methylcyclohexyl, ethylcyclohexyl, butylcyclohexyl, tert.-butylcyclohexyl, dodecylcyclohexyl, ethylcyclopentyl or butylcyclopentyl and $C_6$–$C_{14}$-cycloalkylalkyl radicals G are, for example, cyclohexylmethyl, cyclohexylethyl, cyclohexylbutyl, cyclohexylhexyl, cyclohexyloctyl, cyclopentylpropyl or cyclopentylhexyl.

$C_1$–$C_{18}$-Alkyl radicals G, substituted by $C_7$–$C_{10}$-alkylphenoxy, can be, for example, p-methylphenoxymethyl, p-methylphenoxyethyl, p-methylphenoxypropyl, p-tert.-butylphenoxymethyl, p-tert.-butylphenoxyethyl, 2,4-dimethylphenoxymethyl, 2,4-dimethylphenoxyethyl, 2,4-di-tert.-butylphenoxyethyl, 2,6-di-tert.-butylphenoxymethyl or 2,4,6-trimethylphenoxyethyl.

$C_2$–$C_{12}$-Alkyl radicals G interrupted by —O—, —S—, —SO— or —SO$_2$— are, for example, one of the following radicals: methoxymethyl, 2-butoxyethyl, 2-octyloxyethyl, isopropoxymethyl, 3-butylthiopropyl, 2-decylthioethyl, 2-(isohexylsulfinyl)-ethyl, 2-(butylsulfonyl)-ethyl or 2-(ethylsulfonyl)-propyl.

If $R_2$ is a group of the formula V or of the formula VI, and if $R_{16}$ is or contains a group of the formula VII or of the formula IX, not more than two groups of the formula VII may be present in total in the compound of the formula I.

Those colour-photographic recording materials are preferred which contain, as the light stabiliser, at least one compound of the formula X

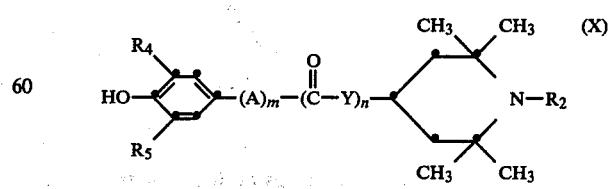

in which $R_1$ is hydrogen or methyl, $R_4$ and $R_5$ independently of one another are $C_1$–$C_4$-alkyl and additionally $R_4$ can also be hydrogen or a group of the formula Xa

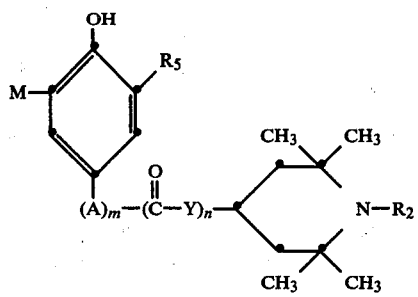

(Xa)

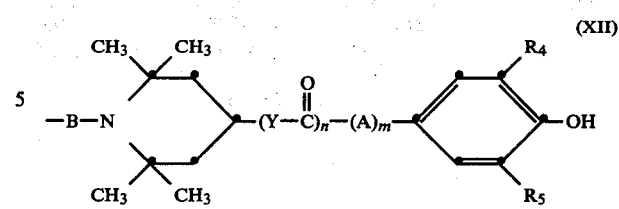

(XII)

in which A, R$_4$, R$_5$, Y, n and m are as defined for these preferred compounds and B is a group —(CH$_2$)$_r$— or —CONH—(CH$_2$)$_r$NHCO—, in which r is one of the numbers 2 to 8, or C$_4$–C$_8$-alkenylene, xylylene or bitolylene, or R$_2$ is one of the groups —SO$_2$R$_{14}$ of —OR$_{15}$, in which R$_{14}$ is C$_1$–C$_4$-alkyl, p-tolyl or phenyl and R$_{15}$ is C$_1$–C$_4$-alkyl, benzyl or a group of the formula L'—CO—, in which L' is as already defined for L in these preferred compounds, and Y is —O— or —N(R$_{16}$)—, in which R$_{16}$ is hydrogen, C$_1$–C$_{12}$-alkyl, cyclohexyl, C$_3$–C$_7$-alkoxyalkyl or a group of the formula XIII in which M is a direct bond, —CH(D$_2$)— or —S— and D$_2$ is hydrogen or C$_1$–C$_8$-alkyl, A is methylene, ethylene or a group —CH$_2$—C(E)(G)—, in which E is cyano, —COCH$_3$ or —COOCH$_3$ and G is hydrogen, C$_1$–C$_{18}$-alkyl, allyl, cyclohexyl, benzyl or one of the two groups of the formulae

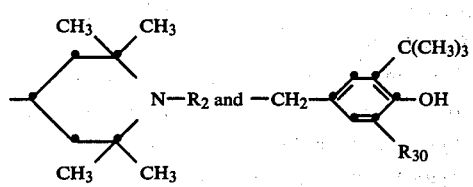

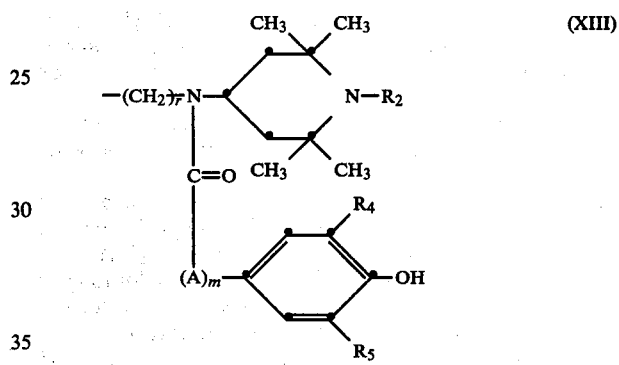

(XIII)

in which R$_{30}$ is methyl or tert.-butyl, or E and G together form a group —CO—(CH$_2$)$_4$—, n and m are as defined above, R$_2$ is hydroxyl, C$_1$–C$_4$-alkyl, allyl, methallyl, propargyl, benzyl, 2-hydroxyethyl, C$_2$–C$_7$-alkoxyalkyl or a group of the formula —(CH$_2$)$_p$—CH(R$_6$)—X$_1$ or —CH(R$_6$)—X$_2$, in which p is one of the numbers 1, 2 or 3, X$_1$ is halogen, cyano, —OR$_7$, —OC(O)R$_7$, —OC(O)N(R$_7$)(R$_8$), —C(O)R$_7$ or —C(O)N(R$_7$)(R$_8$), X$_2$ is halogen, cyano, 1,2-epoxyethyl, —C(O)OR$_7$ or —C(O)N(R$_7$)(R$_8$) and R$_6$ is hydrogen, methyl or phenyl, R$_7$ being hydrogen, C$_1$–C$_8$-alkyl, vinyl, allyl, methallyl, C$_5$–C$_8$-cycloalkyl, phenyl or C$_7$–C$_{10}$-aralkyl and R$_8$ being hydrogen or methyl, or R$_2$ is a group of the formula II, in which L is hydrogen, C$_1$–C$_4$-alkyl, vinyl, allyl, cyclohexyl, phenyl, benzyl, chloromethyl or a group —OR$_9$, in which R$_9$ is C$_1$–C$_8$-alkyl, cyclohexyl, vinyl, allyl or methallyl, or L is a group of the formula III, in which m, A, R$_4$ and R$_5$ are as defined for these preferred compounds, and R$_3$ is hydrogen, or R$_2$ is a group of the formula IV, in which R$_{10}$ and R$_{11}$ independently of one another are C$_1$–C$_{12}$-alkyl, cyclohexyl or phenyl and R$_{11}$ additionally can also be hydrogen, or R$_2$ is a group of the formula XI in which r, m, A, R$_2$, R$_4$ and R$_5$ are as already defined for these preferred compounds.

Those colour-photographic recording materials are particularly preferred which contain, as the light stabiliser, at least one compound of the formula XIV

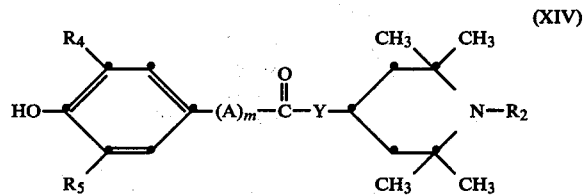

(XIV)

in which m is zero or 1, A is methylene or ethylene, R$_4$ and R$_5$ independently of one another are methyl or tert.-butyl, Y is —O— or —N(R$_{16}$)—, in which R$_{16}$ is hydrogen or C$_1$–C$_8$-alkyl, and R$_2$ is hydroxyl, methyl, allyl, benzyl, 2-hydroxyethyl, acetyl, acryloyl, methoxy, acetoxy or a group of the formula XV

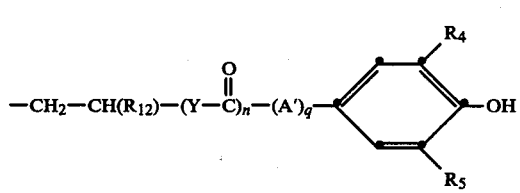

(XI)

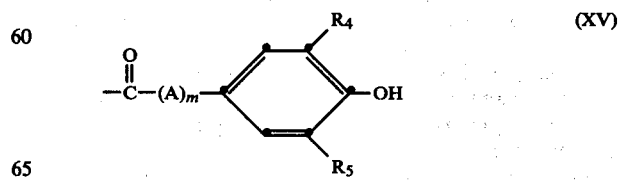

(XV)

in which n, R$_4$, R$_5$ and Y are as defined for these preferred compounds, A' is methylene or a group —CH$_2$—CH(R$_{13}$)—, q is zero or 1, and R$_{12}$ and R$_{13}$ independently of one another are hydrogen or methyl, or R$_2$ is a group of the formula XII in which m, A, R$_4$ and R$_5$ are as defined for these preferred compounds, or is a group of the formula IV, in which $R_{10}$ is $C_1-C_8$-alkyl, cyclohexyl or phenyl and $R_{11}$ is hydrogen, $C_1-C_8$-alkyl or cyclohexyl.

Those colour-photographic recording materials are also particularly preferred which contain, as the light stabiliser, at least one compound of the formula XIV, in which $R_2$ is a group of the formula

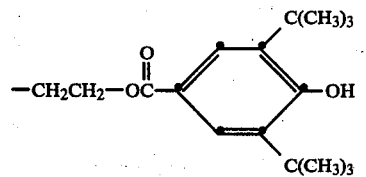

and m, A, $R_4$, $R_5$ and Y are as defined in the last definition of preferred compounds, as well as those colour-photographic recording materials which contain, as the light stabiliser, at least one compound of the formula XIV, in which A is a group $-CH_2-C(E)(G)-$, in which E is cyano, $-COCH_3$ or $-COOCH_3$ and G is hydrogen or one of the two groups of the formulae

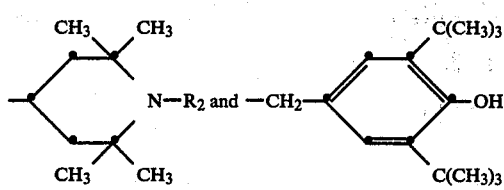

or E and G together form a group $-CO-(CH_2)_4-$, $R_2$ is $-CHO$, acetyl or acryloyl and m, $R_4$, $R_5$ and Y are as defined in the last definition of preferred compounds.

Of particular interest are colour-photographic recording materials which contain, as the light stabiliser, at least one compound of the formula I, in which Y is $-N(R_{16})-$ and n is the number 1. These compounds are novel and, as such, are also a subject of the present invention.

They can be prepared, according to methods known per se, by amidation of known 4-aminopiperidine compounds, approximately in accordance with the equation

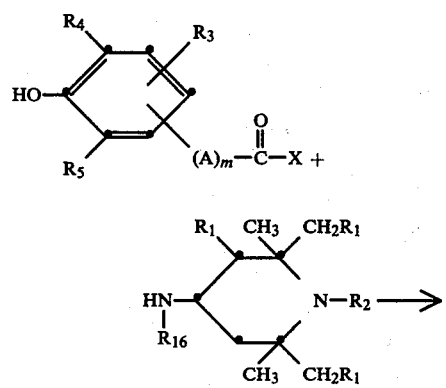

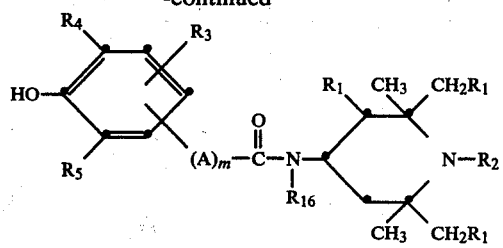

X being chlorine or $-OR$, in which R is methyl or ethyl, and $R_1$, $R_2$, $R_3$, $R_4$, $R_5$, $R_{16}$, A and m being as defined above.

Also of interest are colour-photographic recording materials which contain, as the light stabiliser, at least one compound of the formula I, in which A is a group $-CH_2-C(E)(G)-$, m and n are the number 1 and $R_2$ is $-OH$, $-SO_2R_{14}$, $-OR_{15}$ or a group of the formulae V or VI. These compounds are also novel. They can likewise be prepared by methods known per se and according to the equation

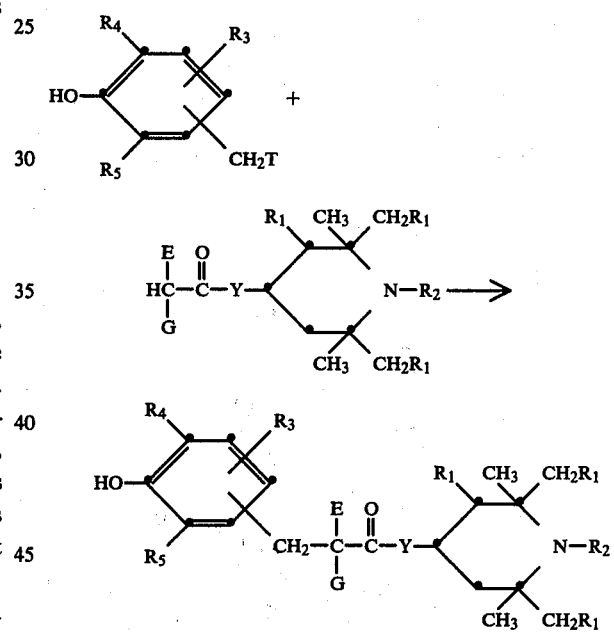

T being a group $-N(R)_2$, $-SC(S)N(R)_2$ or $-OR$, in which R is methyl or ethyl, $R_2$ being $-OH$, $-SO_2R_{14}$, $-OR_{15}$ or a group of the formulae V or VI and $R_1$, $R_3$, $R_4$, $R_5$, E, G and Y being as defined above.

In a variant, it is possible in both cases to prepare the compounds mentioned by known reactions on the ring nitrogen of the compound of the formula

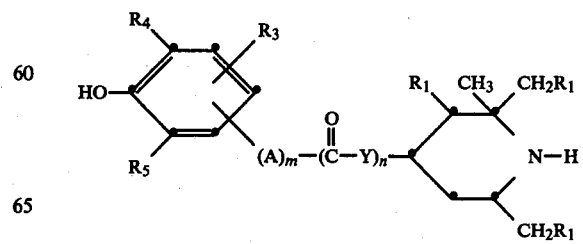

for example by alkylation, acylation or addition.

The starting substances and the other compounds of the formula I are known. If some of these should still be novel, they can be prepared analogously to methods known per se.

Typical representatives of the compounds of the formula I are listed in Tables I to V which follow.

TABLE 1

[Structure: 3,5-di-tert-butyl-4-hydroxyphenyl-CH₂CH₂-C(=O)-Y-(2,2,6,6-tetramethylpiperidin-4-yl)-N-R₂]

| Light stabiliser No. | Y | R₂ |
|---|---|---|
| 1 | —NH— | —CH₃ |
| 2 | —NH— | —CO—CH₃ |
| 3 | —N(C₄H₉)— | —CO—CH₃ |
| 4 | —NH— | —CO—CH=CH₂ |
| 5 | —N(C₄H₉)— | —CO—CH=CH₂ |
| 6 | —O— | —CH₃ |
| 7 | —O— | —CH₂—C₆H₅ (benzyl) |
| 8 | —O— | —CO—CH₃ |
| 9 | —O— | —CO—CH=CH₂ |
| 10 | —O— | —CH₂—CH=CH₂ |
| 11 | —O— | —CH₂CN |
| 12 | >N—C₈H₁₇ | —CO—CH₃ |
| 13 | >N—C₈H₁₇ | —CO—CH=CH₂ |
| 14 | —O— | —CH₂—CH(—O—)CH₂ (glycidyl) |
| 15 | >N(CH₂)₂—N(2,2,6,6-tetramethylpiperidin-4-yl with N—CH₃) bearing CO—(CH₂)₂—(3,5-di-tert-butyl-4-hydroxyphenyl) | —CH₃ |
| 16 | —O— | —CH₃—COOCH₃ |
| 17 | —O— | CO—(CH₂)₂—(3,5-di-tert-butyl-4-hydroxyphenyl) |
| 18 | —O— | —CH₂CH₂OH |
| 19 | —O— | —CH₂—C≡CH |
| 20 | —O— | —CON(C₂H₅)₂ |
| 21 | —O— | —OCH₃ |

TABLE 1-continued

Structure: 3,5-di-tert-butyl-4-hydroxyphenyl-CH₂CH₂-C(=O)-Y-[2,2,6,6-tetramethylpiperidin-4-yl]-N-R₂

| Light stabiliser No. | Y | R₂ |
|---|---|---|
| 22 | —O— | —OCO—(CH₂)₂—(3,5-di-tert-butyl-4-hydroxyphenyl) |
| 23 | —O— | —SO—C₆H₄—CH₃ (p-tolyl) |
| 24 | —O— | —SO₂—C₆H₄—CH₃ (p-tolyl) |
| 25 | (CH₃)₂N(CH₂)₆—N(2,2,6,6-tetramethylpiperidin-4-yl with N—CO—CH=CH₂), with CO—(CH₂)₂—(3,5-di-tert-butyl-4-hydroxyphenyl) on piperidine | —COCH=CH₂ |
| 26 | (CH₃)₂N—(2,2,6,6-tetramethylpiperidin-4-yl with N—CO—CH=CH₂) | —CO—CH=CH₂ |
| 27 | —O— | —CH₂—CH=CH—CH₂—N(2,2,6,6-tetramethylpiperidin-4-yl)—O—CO(CH₂)₂—(3,5-di-tert-butyl-4-hydroxyphenyl) |
| 28 | —O— | —(CH₂)₂—OCO—(CH₂)₂—(3,5-di-tert-butyl-4-hydroxyphenyl) |

TABLE 1-continued

[Structure: 3,5-di-tert-butyl-4-hydroxyphenyl-CH₂CH₂-C(=O)-Y- attached to 2,2,6,6-tetramethylpiperidine with N-R₂]

| Light stabiliser No. | Y | R₂ |
|---|---|---|
| 29 | >N—C₄H₉ | —CH₃ |

TABLE II

[Structure: 3-tert-butyl-4-hydroxy-5-R₄-phenyl-(CH₂)ₙCOO- attached to 2,2,6,6-tetramethylpiperidine with N-R₂]

| Light stabiliser No. | R₄ | n | R₂ |
|---|---|---|---|
| 30 | —H | 2 | —CO—CH=CH₂ |
| 31 | —H | 2 | —CH₃ |
| 32 | —CH₃ | 2 | —CH₃ |
| 33 | —CH₃ | 2 | —CO—CH=CH₂ |
| 34 | —CH₃ | 2 | —CO—CH₃ |
| 35 | —H | 2 | —CO—CH₃ |

TABLE II-continued

| Light stabiliser No. | R₄ | n | R₂ |
|---|---|---|---|
| 36 | —C(CH₃)₃ | 0 | —(CH₂)₂OCO-(3,5-di-tert-butyl-4-hydroxyphenyl) |
| 37 | —C(CH₃)₃ | 0 | —CO—CH=CH₂ |
| 38 | —C(CH₃)₃ | 1 | —CO—CH=CH₂ |

TABLE III

[Structure: 3,5-di-tert-butyl-4-hydroxyphenyl-CH₂-C(E)(G)-COO- attached to 2,2,6,6-tetramethylpiperidine with N-R₂]

| Light stabiliser No. | E | G | R₂ |
|---|---|---|---|
| 39 | —CN | —H | —CHO |
| 40 | —CO—CH₃ | —CH₂-(3,5-di-tert-butyl-4-hydroxyphenyl) | —CO—CH₃ |
| 41 | —COOCH₃ | —CH₂-(3,5-di-tert-butyl-4-hydroxyphenyl) | —CO—CH₃ |

TABLE III-continued
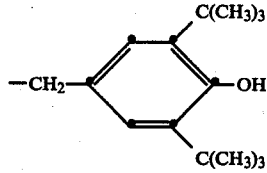
| Light stabiliser No. | E | G | $R_2$ |
|---|---|---|---|
| 42 | —CN | 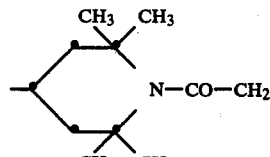 | —CO—CH=CH$_2$ |
| 43 | —CN | 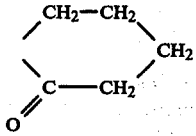 | —CO—CH=CH$_2$ |
| 44 | | 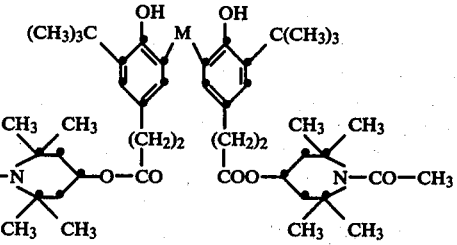 | —CO—CH=CH$_2$ |
TABLE IV
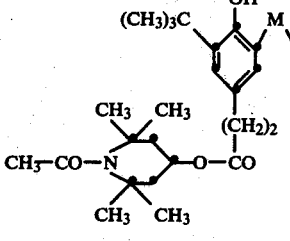
| Light stabiliser No. | M |
|---|---|
| 45 | —S— |
| 46 | —CH$_2$— |
TABLE IV-continued
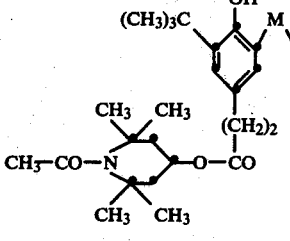
| Light stabiliser No. | M |
|---|---|
| 47 | direct bond |

TABLE V $$\begin{array}{c}
R \\ \diagdown \\ N-(CH_2)_n-N-(CH_2)_n-N \\ \diagup \\ R
\end{array}
\begin{array}{c}
R \\ | \\ \\ \\ R
\end{array}$$

(piperidine rings with CH₃ groups and N–R₂ substituents)

| Light stabiliser No. | n | R | R₂ |
|---|---|---|---|
| 48 | 2 | 3,5-di-tert-butyl-4-hydroxyphenyl–CO–(CH₂)₂– with C(CH₃)₃ groups | –CO–CH₃ |
| 49 | 3 | 3,5-di-tert-butyl-4-hydroxyphenyl–CO–(CH₂)₂– with C(CH₃)₃ groups | –CO–CH=CH₂ |

The compounds of the formula I are scarcely soluble in water and, for this reason, they are dissolved in a low-boiling organic solvent, such as methyl acetate, ethyl acetate, carbon tetrachloride, chloroform, methanol, ethanol, n-butanol, dioxane, acetone or benzene, in a high-boiling organic solvent, such as tricresyl phosphate, dimethylformamide, dimethyl sulfoxide, di-n-butyl phthalate or ethyl N-diphenylcarbamate, or in a solvent mixture consisting of the abovementioned low-boiling and high-boiling organic solvents, the solution obtained is added to a protective colloid solution, such as especially an aqueous gelatine solution, and the mixture is dispersed by means of a colloid mill, a homogeniser or by applying ultrasonics.

The dispersions thus obtained are then used for the preparation of the layers of colour-photographic recording materials. These layers can, for example, be interlayers or protective layers, but especially light-sensitive (for example blue-sensitive, green-sensitive and red-sensitive) silver halide emulsion layers in which, when the exposed recording material is developed, cyan dyes, magenta dyes and yellow dyes are formed from the corresponding colour couplers.

If desired, the light stabiliser can also be applied in the treatment baths which are used after colour development, for example in fixing baths and/or washing baths, but a certain solubility of the compounds of the formula I in alcohols (methanol/ethanol), aqueous alkali and/or water is necessary in that case. If the diffusion transfer method is used, the light stabiliser can be incorporated not only into the customary photographic emulsion layers, but also into a receiving layer.

It is possible to employ any desired cyan couplers, magenta couplers and yellow couplers, which are used for the formation of the said dyes and hence the colour images. They can be dissolved, for example, in an alkaline solution or in a high-boiling organic solvent, these solutions then being dispersed in an aqueous gelatin solution and being incorporated into a photographic silver halide emulsion. They can also be added to colour-photographic developers.

In the photographic recording material according to the present invention, the light stabilisers according to formula I can be combined in the same layer not only with the colour couplers, but additionally also with ultraviolet absorbers.

The silver halide emulsions preferably contain gelatine as the binder, if appropriate as a mixture with other high-molecular natural or synthetic compounds.

The silver halide emulsions can, for example, be silver bromide emulsions, silver chloride emulsions or silver iodide emulsions, or they can also be those emulsions which contain a mixture of silver halides, for example silver bromide/iodide emulsions or silver chloride/bromide emulsions.

The emulsions can be sensitised chemically, and they can also contain customary organic stabilisers and antifogging agents as well as customary plasticisers, for example glycerol. The emulsions can also be hardened with the hardeners customary for gelatine. Moreover, the emulsions can contain customary coating assistants. The emulsions can be applied to customary bases for photographic recording material.

To develop the colour-photographic recording material, the customary developer baths can be used. As a rule, these contain a developer substance of the p-phenylenediamine type, a development retarder, such as potassium bromide, an antioxidant, such as sodium sulfite, and a base, for example an alkali metal hydroxide or alkali metal carbonate. The developing baths can also contain a customary anti-fogging agent and complexing agents.

The light stabilisers to be used according to the invention are in certain cases also suitable for protecting colour-photographic layers, in which the dyes are incorporated directly into the emulsion and the image is produced by selective bleaching.

The quantity of light stabiliser, if appropriate in combination with a customary ultraviolet absorber, can vary within wide limits and is approximately within the range from 1 to 2,000 mg, preferably 1 to 800 and in particular 400 mg, per m² of the layer into which it is (or they are) incorporated.

If the photographic material contains an agent which absorbs UV light, this agent can be present in the same layer or in the adjacent layer.

The ultraviolet absorber can be present in one layer, together with the light stabiliser, or in an adjacent layer. The weight ratio between a customary ultraviolet absorber and the light stabiliser of the formula I is about (5–10):1, and the molar ratio is about (10–20):1. Examples of ultraviolet absorbers are compounds of the benzophenone, acrylonitrile, thiazolidone, benzotriazole, oxazole, thiazole and imidazole type.

The colour images obtained with the recording material according to the invention by exposure and development display very good lightfastness to visible and ultraviolet light. The compounds of the formula I are virtually colourless, so that there is no discolouration of the images: additionally, they are well compatible with the customary photographic additives present in the individual layers; due to their high effectiveness, the quantity in which they are used can be reduced, and they are thus prevented from precipitating or crystallising out, when the are incorporated as an organic solution into the aqueous binder emulsions which are used for the preparation of photographic layers. The individual processing steps, necessary after the exposure of the photographic recording material, for the production of the colour images are not adversely affected by the light stabilisers. Moreover, the formation of so-called abrasion fog, which frequently occurs in the case of blue-sensitive emulsions, can be largely suppressed. This abrasion fog can, for example, occur if mechanical stresses, for example turning, bending or rubbing, are exerted on photographic materials (silver halide emulsion layers present on a base of natural or synthetic materials) during manufacture or during treatment before development (T. H. James, The Theory of the Photographic Process, 4th edition, Macmillan, New York, N.Y. 1977, pages 23 et seq. and pages 166 et seq.).

The examples which follow explain the present invention, without restricting it.

Preparation Examples

EXAMPLE 1

4.1 g of 2,2,6,6-tetramethylpiperidinyl-4-β-(3,5-di-tert.-butyl-4-hydroxyphenyl)-propionamide, 2.8 g of methyl iodide and 6.5 g of anhydrous potassium carbonate are heated under reflux in 100 ml of acetone for four hours. The acetone is evaporated off and the residue is dissolved in 150 ml of ether, washed with water and dried. After evaporation of the solvent, a yellow oil which crystallises from acetonitrile is obtained. This gives 2.6 g (60%) of 1,2,2,6,6-pentamethylpiperidinyl-4-β-(3,5-di-tert.-butyl-4-hydroxyphenyl)-propionamide as colourless crystals having a melting point of 132°–134° C. (light stabiliser 1).

EXAMPLE 2

4.1 g of 2,2,6,6-tetramethylpiperidinyl-4-β-(3,5-di-tert.-butyl-4-hydroxyphenyl)-propionamide are stirred at 90° C. in 80 ml of acetic anhydride for twelve hours. The solvent is evaporated off in vacuo, and the residue is dissolved in 50 ml of methanol and the solution is slowly added dropwise to 150 ml of 10% sodium chloride solution. The solid is filtered off with suction, dried at 50° C. and dissolved in 50 ml of acetone. The acetone solution is clarified by filtration, diluted with 150 ml of ether and cooled to 0° C., and the precipitate obtained is filtered off with suction. This gives 3.1 g (69%) of 1-acetyl-2,2,6,6-tetramethylpiperidinyl-4-β-(3,5-di-tert.-butyl-4-hydroxyphenyl)-propionamide as colourless crystals having a melting point of 130°–132° C. (light stabiliser 2).

EXAMPLE 3

4.7 g of 2,2,6,6-tetramethylpiperidinyl-4-β-(3,5-di-tert.-butyl-4-hydroxyphenyl)-N-butyl-propionamide are stirred at 90° C. in 80 ml of acetic anhydride for twelve hours. The solvent is evaporated off in vacuo, and the orange-coloured oil is heated in 60 ml of petroleum ether at 50° C. for ten minutes. The precipitate is filtered off with suction, washed with petroleum ether and dried at 50° C. This gives 3.5 g (68%) of 1-acetyl-2,2,6,6-tetramethylpiperidinyl-4-β-(3,5-di-tert.-butyl-4-hydroxyphenyl)-N-butyl-propionamide as a colourless powder having a melting point of 133°–135° C. (light stabiliser 3).

EXAMPLE 4

4.1 g of 2,2,6,6-tetramethylpiperidinyl-4-β-(3,5-di-tert.-butyl-4-hydroxyphenyl)-propionamide are dissolved in 150 ml of acetonitrile. 1.5 g of triethylamine are added and the solution is warmed to 60° C. 1.0 g of acrylic acid chloride is added dropwise and the mixture is stirred for one further hour after the addition. The reaction mixture is filtered and the filtrate is evaporated. After purification by column chromatography, 2.0 g of 1-acryloyl-2,2,6,6-tetramethylpiperidinyl-4-β-(3,5-di-tert.-butyl-4-hydroxyphenyl)-propionamide having a melting point of 149° to 151° C. are obtained (light stabiliser 4).

EXAMPLE 5

The procedure described in Example 4 is repeated, using the corresponding amount of 2,2,6,6-tetramethyl-piperidinyl-4-β-(3,5-di-tert.-butyl-4-hydroxyphenyl)-N-butylpropionamide. 1-Acryloyl-2,2,6,6-tetramethyl-piperidinyl-4-β-(3,5-di-tert.-butyl-4-hydroxyphenyl)-N-butylpropionamide having a melting point of 148° to 149° C. is obtained (light stabiliser 5).

EXAMPLE 6

10.8 g of 2,2,6,6-tetramethyl-4-piperidinyl cyanoacetate and 35 g of 2,6-di-tert.-butyl-4-hydroxybenzyl N,N-diethyl-dithiocarbamate are introduced into 150 ml of isopropanol and the mixture is heated to 50° C. At this temperature, a solution of 3.8 g of sodium hydroxide in 20 ml of water is added dropwise in the course of 30 minutes. The light-brown solution is further stirred at 50°–60° C. and then refluxed for 1.5 hours. The green solution is cooled to room temperature, 200 ml of water are added and the solution is then cooled to 5° C. The light-yellow product which has precipitated is filtered off with suction, washed with cold isopropanol (aqueous) and dried. Melting point 174° C. This product is then reacted, as described in Example 4, with acryloyl chloride to give 1-acryloyl-2,2,6,6-tetramethylpiperi-din-4-yl α-(3,5-di-tert.-butyl-4-hydroxybenzyl)-α- cyano-β-(3,5-di-tert.-butyl-4-hydroxyphenyl)-propionate. Melting point 188°–190° C. (Light stabiliser No. 42).

Application Examples

EXAMPLE 7a AND b 0.087 g of the yellow coupler of the formula

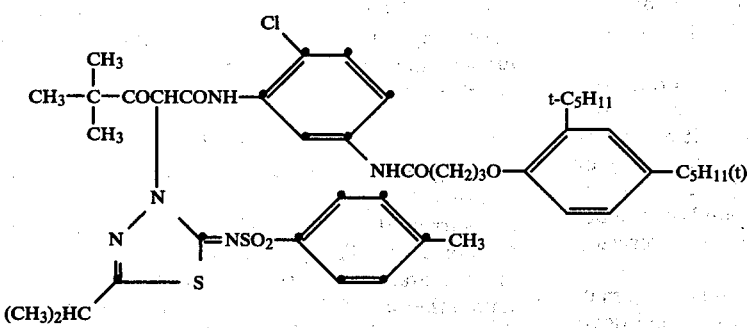

and 0.026 g of one of the light stabilisers indicated in the tables which follow are dissolved in 2.0 ml of a mixture of tricresyl phosphate and ethyl acetate (1.5 g in 100 ml). To this solution, 7.0 ml of a 6% gelatine solution, 0.5 ml of an 8% solution of the wetting agent of the formula

in (3:4) isopropanol/water and 0.5 ml of water are added, and the whole is emulsified ultrasonically for 5 minutes at a power of 100 watt.

2.0 ml of a silver bromide emulsion having a silver content of 6.0 g per liter, 0.7 ml of a 1% aqueous solution of the hardener of the formula

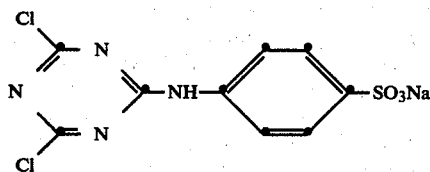

and 3.8 ml of water are added to 2.5 ml of the emulsion thus obtained, and the mixture is adjusted to a pH value of 6.5 and coated onto subbed, plastic-coated, white paper mounted on a glass plate.

After solidification, the paper is dried at room temperature in a circulating-air oven.

After 3 days, samples cut to 35×180 mm are exposed behind a step wedge at 3,000 lux×seconds and then processed by the Kodak Ektaprint 2 ® process.

(a) One part of the yellow wedges thus obtained is irradiated in an Atlas Weather-O-meter with a 2,500 W xenon lamp behind a UV filter (Kodak 2C) with 63 KJoule/cm² and a second part is irradiated with 168 KJoule/cm² (one further comparative sample of each does not contain any light stabiliser).

The table shows the percentage decrease in density, the original density being 1.0:

| Light stabiliser No. | With UV filter Density loss at 440 nm in percent (D = 1.0), quantity of light | |
|---|---|---|
| | 63 KJ/cm² | 168 KJ/cm² |
| — | 13 | 28 |
| 9 | 5 | 13 |
| 27 | 5 | 15 |
| 28 | 5 | 12 |
| 29 | 5 | 13 |
| 36 | 5 | 13 |

(b) A part of the yellow wedges obtained is irradiated as described under (a) but without a UV filter, with 21 KJoule/cm² and a further part is irradiated, likewise without a UV filter, with 63 KJoule/cm² (one further comparative sample of each does not contain any light stabiliser).

The table shows the percentage decrease in density, the original density being 1.0:

| Light stabiliser No. | Without UV filter Density loss at 440 nm in percent (D = 1.0), quantity of light | |
|---|---|---|
| | 21 KJ/cm² | 63 KJ/cm² |
| — | 14 | 37 |
| 4 | 3 | 16 |
| 36 | 5 | 15 |

EXAMPLE 8

0.025 g of the cyan coupler of the formula

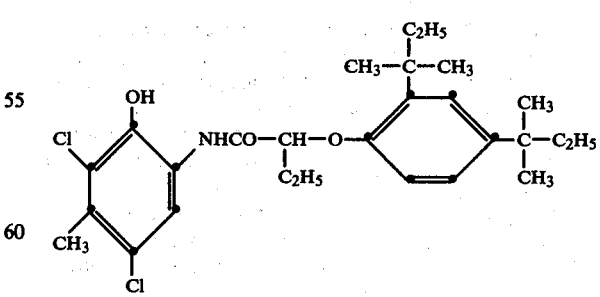

and 0.025 g of a light stabiliser from the table which follows are dissolved in 1 ml of a mixture of tricresyl phosphate and ethyl acetate (1.5 g in 100 ml). To this solution, 7.0 ml of a 6% gelatine solution, 0.5 ml of an 8% solution of the wetting agent of the formula

in (3:4) isopropanol/water and 0.5 ml of water are added, and the whole is emulsified ultrasonically for 5 minutes at a power of 100 watt.

2.0 ml of a silver bromide emulsion having a silver content of 6.0 g per liter, 0.7 ml of a 1% aqueous solution of the hardener of the formula

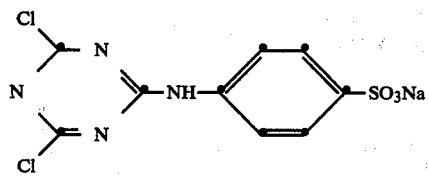

and 3.8 ml of water are added to 2.5 ml of the emulsion thus obtained, and the mixture is adjusted to a pH value of 6.5 and coated onto subbed, plastic-coated, white paper mounted on a glass plate.

After solidification, the paper is dried at room temperature in a circulating-air oven.

Analogously to the procedure described in Example 7a and b, layers are prepared, exposed and processed.

The wedges obtained are stored in an air-conditioned cabinet at 60° C. and 70% relative humidity. The table which follows shows the percentage decrease in the cyan density, the original density being 1.0 in the red (measured by means of a Densitometer®TR 924 Status A, from Messrs. Macbeth).

| Light stabiliser No. | Density loss in the red in percent (D = 1.0, 60° C./70% relative humidity) | |
|---|---|---|
| | 14 days | 28 days |
| — | 32 | 46 |
| 36 | 15 | 25 |
| 40 | 16 | 26 |

What is claimed is:

1. A colour-photographic recording material which, in at least one light-sensitive silver halide emulsion layer, an interlayer and/or a protective layer, contains a light stabilising amount of at least one polyalkylpiperidine compound as a light stabiliser, wherein the polyalkylpiperidine compound is of the formula I

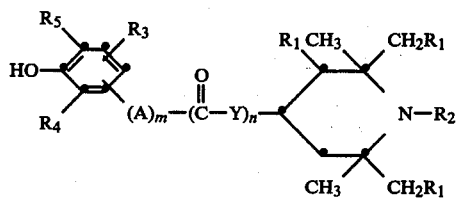

in which $R_1$ and $R_3$ independently of one another are hydrogen or methyl, $R_2$ is hydroxyl, $C_1$-$C_{12}$-alkyl, $C_3$-$C_{12}$-alkenyl, $C_3$-$C_4$-alkynyl, 2-hydroxyethyl, $C_2$-$C_{11}$-alkoxyalkyl, $C_7$-$C_{14}$-aralkyl or a group of the formula $-(CH_2)_p-CH(R_6)-X_1$ or $-CH(R_6)-X_2$, in which p is one of the numbers 1, 2 or 3, $X_1$ is halogen, cyano, $-OR_7$, $-OC(O)R_7$, $-OC(O)N(R_7)(R_8)$, $-C-$ $(O)OR_7$ or $-C(O)N(R_7)(R_8)$, $X_2$ is halogen, cyano, 1,2-epoxyethyl, $-C(O)OR_7$ or $-C(O)N(R_7)(R_8)$ and $R_6$ is hydrogen, methyl or phenyl, $R_7$ being hydrogen, $C_1$-$C_{12}$-alkyl, $C_2$-$C_{12}$-alkenyl, $C_3$-$C_{12}$-cycloalkyl, phenyl, $C_7$-$C_{14}$-alkaryl or $C_7$-$C_{14}$-aralkyl and $R_8$ being hydrogen or $C_1$-$C_4$-alkyl, or $R_7$ and $R_8$, together with the nitrogen atom to which they are bonded, forming a 5-membered or 6-membered heterocyclic ring, or $R_2$ is a group of the formula II

in which L is hydrogen, $C_1$-$C_{12}$-alkyl, $C_2$-$C_{12}$-alkenyl, $C_3$-$C_4$-alkynyl, $C_3$-$C_{12}$-cycloalkyl, $C_7$-$C_{14}$-alkaryl, $C_7$-$C_{14}$-aralkyl, chloromethyl, unsubstituted phenyl, phenyl which is substituted by two $C_1$-$C_4$-alkyls and one hydroxyl, or a group $-OR_9$, in which $R_9$ is $C_1$-$C_{12}$-alkyl, cyclohexyl, $C_2$-$C_{12}$-alkenyl, benzyl or phenyl, or L is a group of the formula III

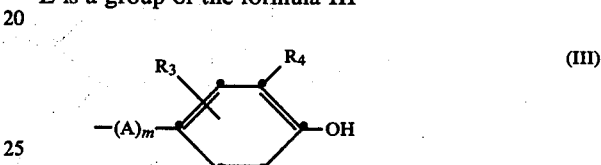

or $R_2$ is a group of the formula IV

in which $R_{10}$ and $R_{11}$ independently of one another are $C_1$-$C_{12}$-alkyl, $C_3$-$C_{12}$-alkenyl, $C_3$-$C_{12}$-cycloalkyl, phenyl, $C_7$-$C_{14}$-alkaryl or $C_7$-$C_{14}$-aralkyl and $R_{11}$ additionally can also be hydrogen, or $R_2$ is a group of the formula V

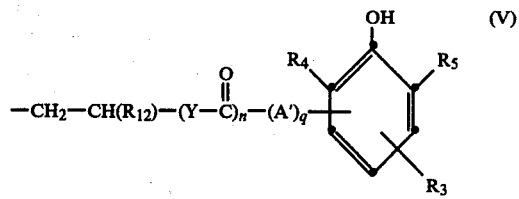

in which A' is methylene or a group $-CH_2-CH(R_{13})-$ and q is zero or 1, and $R_{12}$ and $R_{13}$ independently of one another are hydrogen, methyl, ethyl, phenoxymethyl or phenyl, or $R_2$ is a group of the formula VI

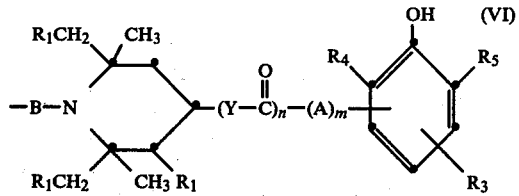

in which B is a group $C_rH_{2r}$, in which r is a number from 2 to 12, or is $C_4$-$C_8$-alkenylene, $C_4$-$C_8$-alkynylene, phenylene, xylylene, bitolylene, $C_5$-$C_{12}$-cycloalkylene or a group $-CONH-B_1-NHCO-$, in which $B_1$ is a group $C_rH_{2r}$, phenylene, naphthylene, tolylene or a group of the formulae

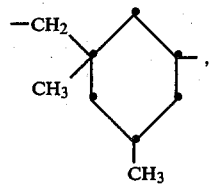

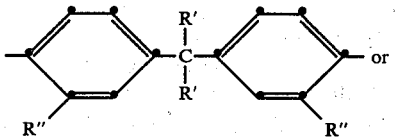

or

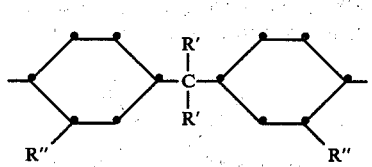

in which R' is hydrogen, methyl or ethyl, R" is hydrogen or methyl and r is as defined above, or $R_2$ is one of the groups $—S(O)_zR_{14}$ or $—OR_{15}$, in which z is the number 1 or 2, $R_{14}$ is $C_1$-$C_{12}$-alkyl, $C_7$-$C_{14}$-alkaryl or phenyl and $R_{15}$ is $C_1$-$C_{12}$-alkyl, $C_3$-$C_{12}$-alkenyl, $C_7$-$C_{14}$-aralkyl or a group of the formula L'—CO—, in which L' is as defined above for L, $R_4$ and $R_5$ independently of one another are $C_1$-$C_{12}$-alkyl, $C_3$-$C_{12}$-cycloalkyl, $C_7$-$C_{14}$-aralkyl, $C_7$-$C_{14}$ alkaryl or phenyl and $R_4$ can additionally also be hydrogen or a group of the formula Ia

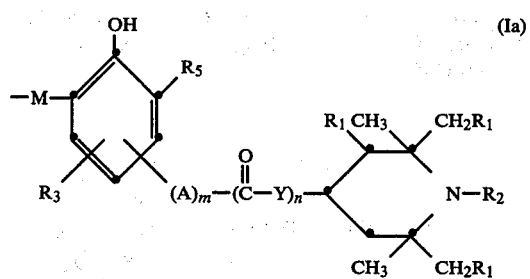
(Ia)

in which $R_1$, $R_2$, $R_3$, $R_5$, A, Y, m and n are as defined herein and M is a direct bond,

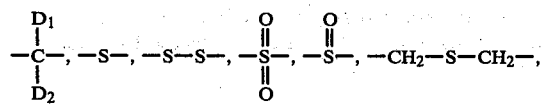

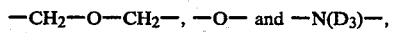
$—CH_2—O—CH_2—$, $—O—$ and $—N(D_3)—$, and $D_1$ and $D_2$ independently of one another are hydrogen, $C_1$-$C_{18}$-alkyl, alkyl interrupted by 1 to 3 —S— or phenyl, or $D_1$ and $D_2$, together with the C atom linking them, form a 5-membered or 6-membered aliphatic ring and $D_3$ is hydrogen, $C_1$-$C_{18}$-alkyl or phenyl, Y is —O— or $—N(R_{16})—$, in which $R_{16}$ is hydrogen, $C_1$-$C_{18}$-alkyl, $C_3$-$C_{12}$-alkenyl, $C_3$-$C_{12}$-cycloalkyl, phenyl, $C_7$-$C_{14}$-alkaryl, $C_7$-$C_{14}$-aralkyl, $C_3$-$C_{11}$-alkoxyalkyl, a group of the formula VII

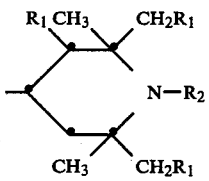
(VII)

or a group —Z—D, in which Z is a $—(CH_2)_s$ group unsubstituted or substituted by a methyl group, s being one of the numbers 2 to 4 and D being hydroxyl, $—OR_7$ or $—N(R_{18})(R_{19})$, in which $R_{17}$ and $R_{18}$ are hydrogen, $C_1$-$C_{12}$-alkyl, $C_3$-$C_{12}$-cycloalkyl or a group of the formula VIII

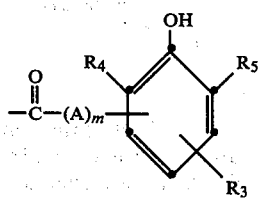
(VIII)

and $R_{17}$ additionally can also be a group of the formula VII, $R_{19}$ is hydrogen, $C_1$-$C_{12}$-alkyl, $C_3$-$C_{12}$-cycloalkyl or a group of the formula IX

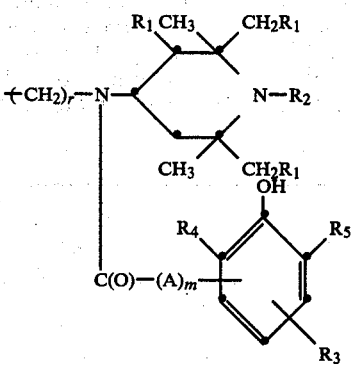
(IX)

or $R_{18}$ and $R_{19}$, together with the nitrogen atom to which they are bonded, form a 5-membered or 6-membered heterocyclic ring, or $R_{16}$ is a group of the formula IXa

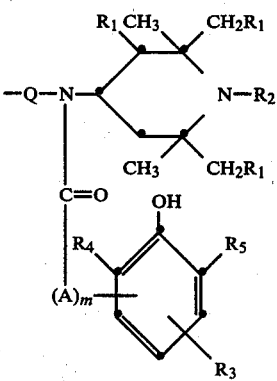
(IXa)

in which Q is as defined above for B, n and m independently of one another are zero or 1, and A is methylene or a group $—CH_2—CH(R_{20})—$ or $—CH_2—C(E)(G)—$, in which $R_{20}$ is hydrogen, methyl, ethyl, phenoxymethyl or phenyl, E is cyano or a group —C(O)OR$_{21}$, —C(O)R$_{22}$, —SO$_2$R$_{22}$, —P(O)—(OR$_{23}$)$_2$, —C(O)NR$_{24}$R$_{25}$ or —CHO, in which $R_{21}$ is $C_1$–$C_4$-alkyl, $R_{22}$ is $C_1$–$C_{12}$-alkyl, $C_7$–$C_{14}$-alkaryl or phenyl, $R_{23}$ is $C_1$–$C_{18}$-alkyl, phenyl or allyl, and $R_{24}$ and $R_{25}$ independently of one another are hydrogen, $C_1$–$C_{18}$-alkyl or phenyl, and G is hydrogen, $C_1$–$C_{18}$-alkyl, $C_3$–$C_{12}$-alkenyl, $C_3$–$C_4$-alkynyl, $C_5$–$C_{12}$-cycloalkyl, $C_6$–$C_{18}$-alkylcycloalkyl, $C_6$–$C_{14}$-cycloalkylalkyl, $C_7$–$C_{14}$-aralkyl, $C_7$–$C_{19}$-alkylaralkyl, phenyl, or $C_1$–$C_{18}$-alkyl which is substituted by phenoxy, $C_7$–$C_{10}$-alkylphenoxy, benzyloxy, cyclohexyloxy, cyano, —COOR$_{26}$, —OCOR$_{27}$ or —P(O)(OR$_{28}$)$_2$, $R_{26}$ being $C_1$–$C_{18}$-alkyl or $C_3$–$C_{12}$-cycloalkyl, $R_{27}$ being $C_1$–$C_{18}$-alkyl, $C_3$–$C_{12}$-cycloalkyl, phenyl, $C_7$–$C_{14}$-aralkyl or a group of the formula III and $R_{28}$ being $C_1$–$C_{18}$-alkyl, allyl or phenyl, or G is $C_2$–$C_{18}$-alkyl interrupted by —O—, —S—, —SO— or —SO$_2$— or a group of the formula

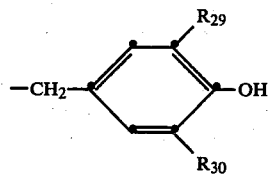

in which $R_{29}$ and $R_{30}$ independently of one another are $C_1$–$C_4$-alkyl and $R_{30}$ additionally can also be hydrogen, or, if E is a group —C(O)R$_{22}$, G and $R_{22}$ together are trimethylene or tetramethylene.

2. A colour-photographic recording material according to claim 1, which contains as the light stabiliser, at least one polyalkylpiperidine compound of the formula X

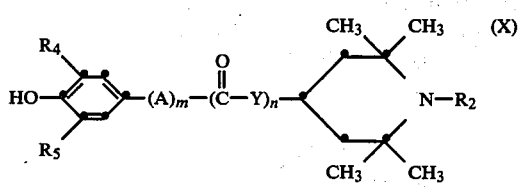

in which $R_1$ is hydrogen or methyl, $R_4$ and $R_5$ independently of one another are $C_1$–$C_4$-alkyl and additionally $R_4$ can also be hydrogen or a group of the formula Xa

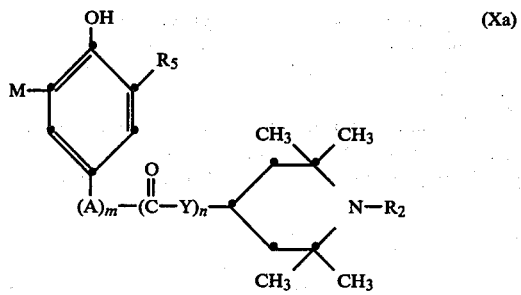

in which M is a direct bond, —CH(D$_2$)— or —S— and D$_2$ is hydrogen or $C_1$–$C_8$-alkyl, A is methylene, ethylene or a group —CH$_2$—C(E)(G)—, in which E is cyano, —COCH$_3$ or —COOCH$_3$ and G is hydrogen, $C_1$–$C_{18}$-alkyl, allyl, cyclohexyl, benzyl or a group of the formula

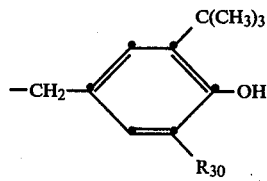

in which $R_{30}$ is methyl or tert.-butyl, or E and G together form a group —CO—(CH$_2$)$_4$—, n and m are as defined in claim 1, $R_2$ is hydroxyl, $C_1$–$C_4$-alkyl, allyl, methallyl, propargyl, benzyl, 2-hydroxyethyl, $C_2$–$C_7$-alkoxyalkyl or a group of the formula —(CH$_2$)$_p$—CH(R$_6$)—X$_1$ or —CH(R$_6$)—X$_2$, in which p is one of the numbers 1, 2 or 3, X$_1$ is halogen, cyano, —OR$_7$, —OC(O)R$_7$, —OC(O)N(R$_7$)(R$_8$), —C(O)R$_7$ or —C(O)N(R$_7$)(R$_8$), X$_2$ is halogen, cyano, 1,2-epoxyethyl, —C(O)OR$_7$ or —C(O)N(R$_7$)(R$_8$) and $R_6$ is hydrogen, methyl or phenyl, $R_7$ being hydrogen, $C_1$–$C_8$-alkyl, vinyl, allyl, methallyl, $C_5$–$C_8$-cycloalkyl, phenyl or $C_7$–$C_{10}$-aralkyl and $R_8$ being hydrogen or methyl, or $R_2$ is a group of the formula II in claim 1, in which L is hydrogen, $C_1$–$C_4$-alkyl, vinyl, allyl, cyclohexyl, phenyl, benzyl, chloromethyl or a group —OR$_9$, in which $R_9$ is $C_1$–$C_8$-alkyl, cyclohexyl, vinyl, allyl or methallyl, or L is a group of the formula III in claim 1, in which m, A, $R_4$ and $R_5$ are as defined in this claim, and $R_3$ is hydrogen, or $R_2$ is a group of the formula IV in claim 1, in which $R_{10}$ and $R_{11}$ independently of one another are $C_1$–$C_{12}$-alkyl, cyclohexyl or phenyl and $R_{11}$ additionally can also be hydrogen, or $R_2$ is a group of the formula XI

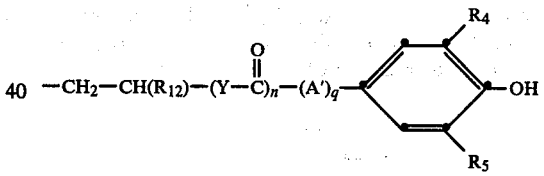

in which n, $R_4$, $R_5$ and Y are as defined in this claim, A' is methylene or a group —CH$_2$—CH(R$_{13}$)—, q is zero or 1, and $R_{12}$ and $R_{13}$ independently of one another are hydrogen or methyl, or $R_2$ is a group of the formula XII

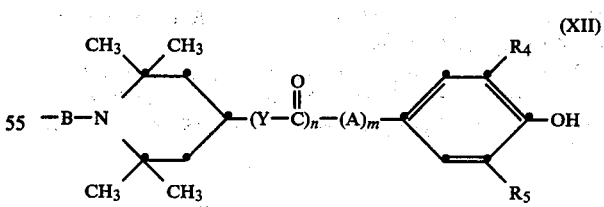

in which A, $R_4$, $R_5$, Y, n and m are as defined in this claim and B is a group —(CH$_2$)$_r$— or —CONH—(CH$_2$)$_r$NHCO—, in which r is one of the numbers 2 to 8, or $C_4$–$C_8$-alkenylene, xylylene or bitolylene, or $R_2$ is one of the groups —SO$_2$R$_{14}$ or —OR$_{15}$, in which $R_{14}$ is $C_1$–$C_4$-alkyl, p-tolyl or phenyl and $R_{15}$ is $C_1$–$C_4$-alkyl, benzyl or a group of the formula L'—CO—, in which L' is as previously defined for L in this claim, and Y is —O— or —N(R$_{16}$)—, in which $R_{16}$ is hydrogen, $C_1-C_{12}$-alkyl, cyclohexyl, $C_3-C_7$-alkoxyalkyl or a group of the formula XIII

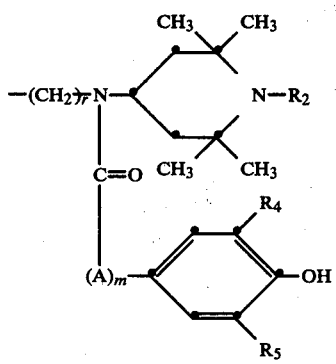

(XIII)

in which r, m, A, $R_2$, $R_4$ and $R_5$ are as previously defined in this claim.

3. A colour-photographic recording material according to claim 1, which contains, as the light stabiliser, at least one polyalkylpiperidine compound of the formula XIV

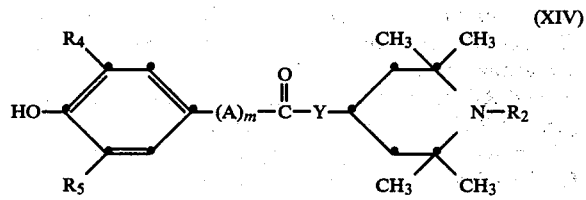

(XIV)

in which m is zero or 1, A is methylene or ethylene, $R_4$ and $R_5$ independently of one another are methyl or tert.-butyl, Y is —O— or —N($R_{16}$)—, in which $R_{16}$ is hydrogen or $C_1-C_8$-alkyl, and $R_2$ is hydroxyl, methyl, allyl, benzyl, 2-hydroxyethyl, acetyl, acryloyl, methoxy, acetoxy or a group of the formula XV

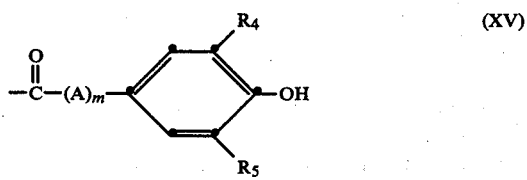

(XV)

in which m, A, $R_4$ and $R_5$ are as defined in this claim, or is a group of the formula IV of claim 1, in which $R_{10}$ is $C_1-C_8$-alkyl, cyclohexyl or phenyl and $R_{11}$ is hydrogen, $C_1-C_8$-alkyl or cyclohexyl.

4. A colour photographic recording material according to claim 1, which contains, as the light stabiliser, at least one polyalkylpiperidine compound of the formula XIV

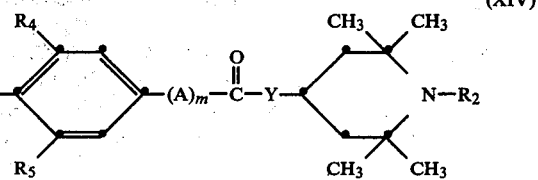

(XIV)

in which $R_2$ is a group of the formula

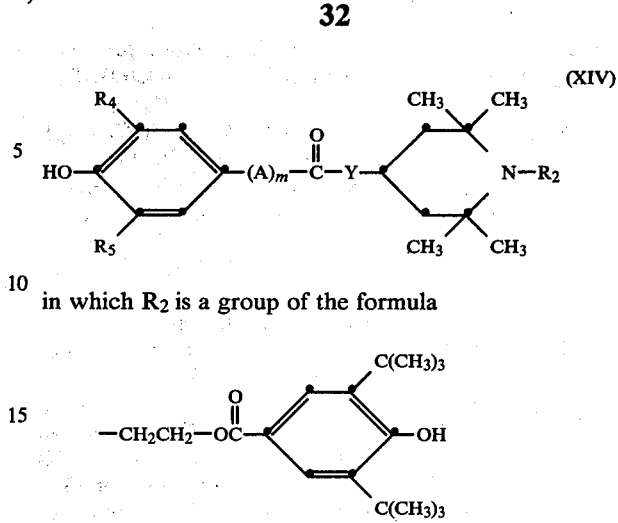

m is 0 or 1, A is methylene or ethylene, $R_4$ and $R_5$ independently of one another are methyl or tert.-butyl, and Y is —O— or —N($R_{16}$)—, in which $R_{16}$ is hydrogen or $C_1-C_8$-alkyl.

5. A colour-photographic recording material according to claim 1, which contains, as the light stabiliser, at least one polyalkylpiperidine compound of the formula XIV

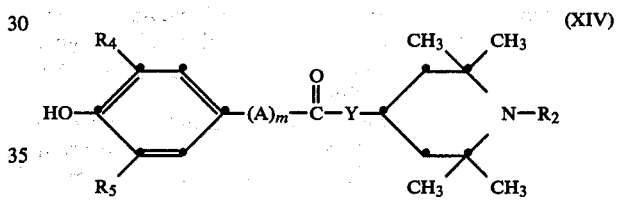

(XIV)

in which A is a group —$CH_2$—C(E)(G)—, in which E is cyano, —$COCH_3$ or —$COOCH_3$ and G is hydrogen or a group of the formula

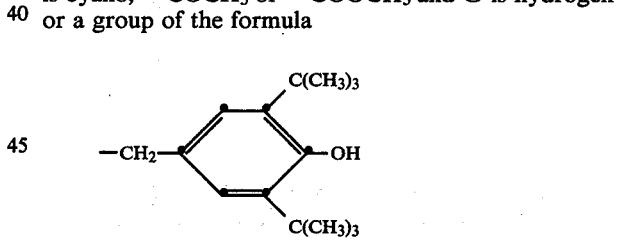

or E and G together form a group —CO—$(CH_2)_4$—, $R_2$ is —CHO, acetyl or acryloyl, m is 0 or 1, $R_4$ and $R_5$ independently of one another are methyl or tert.-butyl, and Y is —O— or —N($R_{16}$)—, in which $R_{16}$ is hydrogen or $C_1-C_8$-alkyl.

6. A colour-photographic recording material according to claim 1, which contains, as the light stabiliser, the polyalkylpiperidine compound of the formula

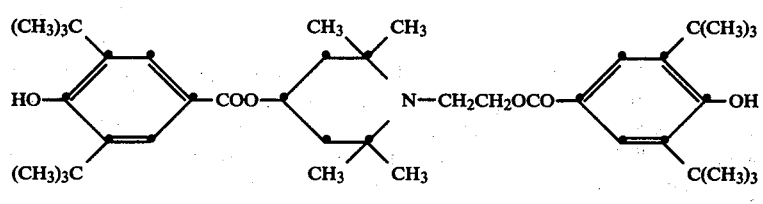

7. A colour-photographic recording material according to claim 1, which contains, as the light stabiliser, the polyalkylpiperidine compound of the formula

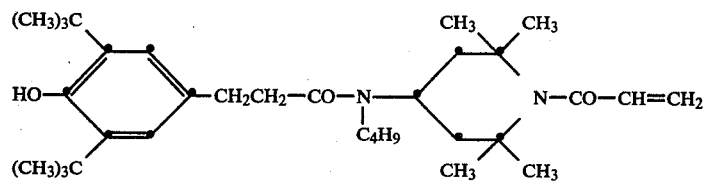

8. A colour-photographic recording material according to claim 1, which contains, as the light stabiliser, the polyalkylpiperidine compound of the formula

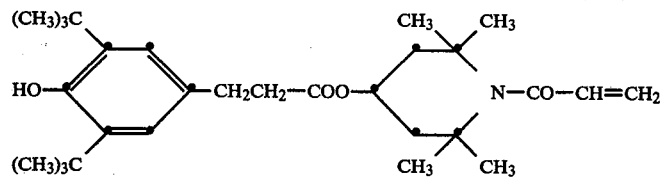

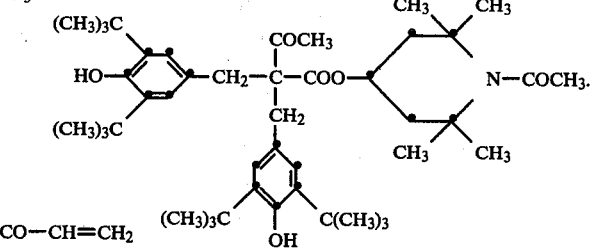

9. A colour-photographic recording material according to claim 1, which contains, as the light stabiliser, the polyalkylpiperidine compound of the formula

* * * * *

UNITED STATES PATENT AND TRADEMARK OFFICE
CERTIFICATE OF CORRECTION

PATENT NO. : 4,452,884

DATED : June 5, 1984

INVENTOR(S) : DAVID G. LEPPARD and JEAN RODY

Page 1 of 3

It is certified that error appears in the above-identified patent and that said Letters Patent is hereby corrected as shown below:

On the cover page of the patent, immediately following the title, correct the listing of inventors to read:

--[75]  Inventor:  David G. Leppard, Rheinfelden; Jean Rody, Riehen, both of Switzerland --.

Column 4, line 56, change "-P(O)- -(OR$_{23}$)$_2$" to read -- -P(O)(OR$_{23}$)$_2$--.

Columns 11 and 12, in Table 1, Light Stabilizer No. 17, correct the formula under the column headed R$_2$ to read as follows:

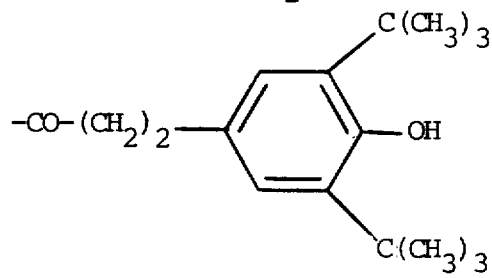

Column 17, Table III-continued, Light Stabilizer No. 44, reposition the formula presently positioned under the column headed "G" to position it between the columns headed "E" and "G".

UNITED STATES PATENT AND TRADEMARK OFFICE
CERTIFICATE OF CORRECTION

PATENT NO. : 4,452,884

DATED : June 5, 1984

INVENTOR(S) : DAVID G. LEPPARD and JEAN RODY

It is certified that error appears in the above-identified patent and that said Letters Patent is hereby corrected as shown below:

Column 25, correct the formula appearing between lines 15 and 20 to read as follows:

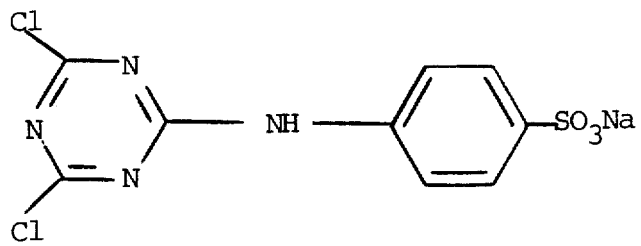

Column 29, line 3, change "-P(O)- -(OR$_{23}$)$_2$" to read -- -P(O)(OR$_{23}$)$_2$ --.

UNITED STATES PATENT AND TRADEMARK OFFICE
CERTIFICATE OF CORRECTION

PATENT NO. : 4,452,884
DATED : June 5, 1984
INVENTOR(S) : DAVID G. LEPPARD and JEAN RODY It is certified that error appears in the above-identified patent and that said Letters Patent is hereby corrected as shown below:

Column 29, correct the formula appearing between lines 50 and 60 to read as follows:

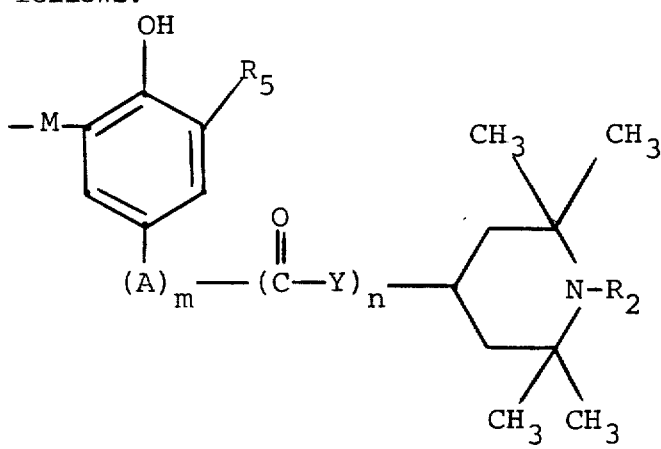

Signed and Sealed this

Ninth Day of April 1985

[SEAL]

Attest:

DONALD J. QUIGG

Attesting Officer     Acting Commissioner of Patents and Trademarks